United States Patent
Ochiai

(10) Patent No.: US 12,420,000 B2
(45) Date of Patent: Sep. 23, 2025

(54) BREAST PUMP

(71) Applicant: Pigeon Corporation, Chuo-ku (JP)

(72) Inventor: Yukifumi Ochiai, Tokyo (JP)

(73) Assignee: Pigeon Corporation, Chuo-ku Tokyo (JP)

( * ) Notice: Subject to any disclaimer, the term of this patent is extended or adjusted under 35 U.S.C. 154(b) by 863 days.

(21) Appl. No.: 17/760,752

(22) PCT Filed: Sep. 20, 2019

(86) PCT No.: PCT/JP2019/037033
§ 371 (c)(1),
(2) Date: Mar. 15, 2022

(87) PCT Pub. No.: WO2021/053818
PCT Pub. Date: Mar. 25, 2021

(65) Prior Publication Data
US 2022/0339332 A1     Oct. 27, 2022

(51) Int. Cl.
*A61M 1/06*     (2006.01)
(52) U.S. Cl.
CPC .............. *A61M 1/06* (2013.01); *A61M 1/062* (2014.02); *A61M 1/069* (2021.05)
(58) Field of Classification Search
CPC ........................................... A61M 1/06-0697
See application file for complete search history.

(56) References Cited

U.S. PATENT DOCUMENTS

2013/0245548 A1* 9/2013 Cook ...................... A61M 1/82
604/74

2017/0072119 A1  3/2017 Aalders et al.
2020/0141504 A1  5/2020 Ochiai et al.
2020/0171223 A1  6/2020 Ochiai et al.

FOREIGN PATENT DOCUMENTS

| JP | 2017509418 A | 4/2017 |
| JP | 2018047043 A | 3/2018 |
| JP | 2019010350 A | 1/2019 |
| WO | 2019004093   | 1/2019 |

OTHER PUBLICATIONS

"European Application Serial No. 19945993.4, Extended European Search Report mailed May 9, 2023", 7 pgs.
International Application No. PCT/JP2019/037033, Search Report mailed May 11, 2019 (English translation), 1 pg.

* cited by examiner

*Primary Examiner* — Courtney B Fredrickson
(74) *Attorney, Agent, or Firm* — Schwegman Lundberg & Woessner, P.A.

(57) ABSTRACT

A breast pump includes a main body, a diaphragm, a handle, a connecting portion, and a volume reduction portion. The main body includes a hood attaching portion attached to the hood, a bottle attaching portion attached to a bottle for collecting milk, and an internal passage extending between the hood attaching portion and the bottle attaching portion. The diaphragm is attached to the internal passage and is configured to generate negative pressure in the internal passage. The connecting portion connects the diaphragm and the handle and is configured to displace the diaphragm in a lifting direction in accordance with movement of the handle. The volume reduction portion is inserted into the internal passage and is configured to reduce a volume of the internal passage.

4 Claims, 6 Drawing Sheets

BREAST PUMP

This application is a U.S. National Stage Filing under 35 U.S.C. 371 from International Application No. PCT/JP2019/037033, filed on Sep. 20, 2019, and published as WO 2021/053818 A1 on Mar. 25, 2021, which is incorporated by reference herein in its entirety.

TECHNICAL FIELD

The present disclosure relates to a breast pump for manually pumping milk.

BACKGROUND ART

Patent Literature 1 describes an example of a breast pump that includes a main body, a diaphragm, and a handle. A hood and a bottle are attached to the main body. The hood is fitted to a breast, and the bottle collects milk. The diaphragm is arranged in an internal passage that connects the bottle and a milking port in the hood. The diaphragm causes the pressure of the internal passage to become negative. The handle is manually operated to move the diaphragm. When the diaphragm is lifted by operating the handle, the volume of the internal passage is increased so that the pressure of the internal passage becomes negative in the breast pump. The negative pressure collects the milk extracted from the nipple in a temporary reservoir that is part of the internal passage. When the internal passage returns from the negative pressure state to a normal pressure state, a valve of the temporary reservoir opens and the milk flows from the temporary reservoir into the bottle.

It is important that hygiene be maintained in the internal passage through which the pumped milk flows, and the internal passage should be cleaned after use. For cleaning, parts such as the hood, bottle, and diaphragm are removed from the main body and cleaned with the hands or scrubbed with a brush.

CITATION LIST

Patent Literature

Patent Literature 1: Japanese Patent Application Laid-Open No. 2019-10350

SUMMARY OF INVENTION

Technical Problem

In the breast pump, the handle is operated to deform the diaphragm and cause the pressure of the internal passage to be negative. The amount the diaphragm is displaced is in accordance with the amount the handle is manual operated. Thus, the displacement amount of the handle is not large. When the internal passage has a larger volume, the pressure changed by displacement of the diaphragm will be smaller. This will lower the milk-pumping efficiency. Accordingly, the internal passage is usually narrow and small in diameter and thus difficult to clean with fingers and the like.

An objective of the present disclosure is to provide a breast pump that allows the internal passage to be cleaned easily without lowering the milk-pumping efficiency.

Solution to Problem

A breast pump that solves the above problem includes a main body, a diaphragm, a handle, a connecting portion, and a volume reduction portion. The main body includes a hood attaching portion, a bottle attaching portion, and an internal passage. A hood is attached to the hood attaching portion. The hood is fitted to a breast and includes a milking port. A bottle is attached to the bottle attaching portion and collects milk. The internal passage extends between the hood attaching portion and the bottle attaching portion. The diaphragm is attached to the internal passage and is configured to generate negative pressure in the internal passage. The handle is manually operated. The connecting portion connects the diaphragm and the handle and is configured to displace the diaphragm in a lifting direction in accordance with movement of the handle. The volume reduction portion is inserted into the internal passage and is configured to reduce a volume of the internal passage.

With the above structure, even though the internal passage is increased in diameter to be cleaned easily, the volume reduction portion is inserted into the portion where the diameter is increased. Thus, the volume of the internal passage is not increased, and decreases in the milk-pumping efficiency are minimized.

In the breast pump, the connecting portion may be a lift plate that includes a plate portion and a connection projection. The plate portion is arranged on an inner surface of the diaphragm. The connection projection extends from the plate portion through the diaphragm, projects out of an outer surface of the diaphragm located at a side opposite to the inner surface, and is connected with the handle. The volume reduction portion may be arranged on the plate portion.

With this structure, the volume reduction portion is arranged on the lift plate. This facilitates processes like cleaning and assembling/disassembling. The volume reduction portion is moved in cooperation with the movement of the handle.

In the above breast pump, the handle may be pivotally attached to the main body and configured to lift the diaphragm using the connecting portion in a direction intersecting a bottle axis that extends in a height direction of the bottle. With this structure, the volume reduction portion is moved in the internal passage in accordance with the pivoting operation of the handle.

In the above breast pump, the internal passage may include a negative pressure passage closed by the diaphragm, and the volume reduction portion may be inserted in the negative pressure passage. With this structure, the volume reduction portion reduces the volume of the negative pressure generation passage.

In the above breast pump, the breast pump may include a gap formed between an inner circumferential surface of the negative pressure generation passage and an outer circumferential surface of the volume reduction portion. With this structure, the gap allows the volume reduction portion to be smoothly reciprocated in the negative pressure generation passage.

Advantageous Effects of Invention

The present invention allows the internal passage to be cleaned easily w % bile minimizing decreases in the milk-pumping efficiency.

DESCRIPTION OF EMBODIMENT

A breast pump will now be described with reference to FIGS. 1 to 6.

Figure 1:
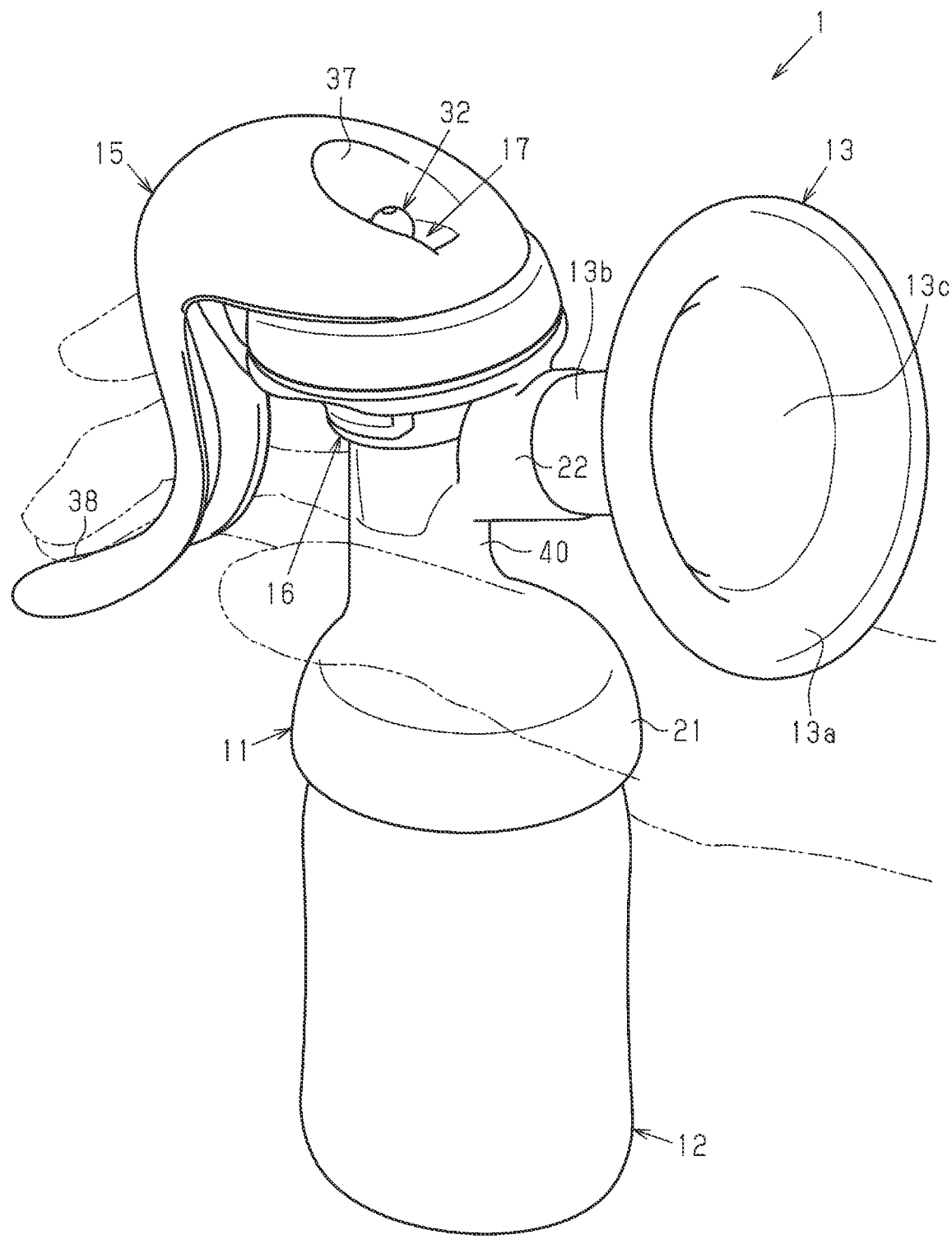
FIG. 1 is a perspective view of a breast pump.

As shown in FIG. 1, a breast pump 1 is a manual breast pump that is sized so that a user can operate it with one hand. The breast pump 1 includes a main body 11, a bottle 12, a hood 13, a diaphragm 14 (refer to FIG. 2), a handle 15, a handle base 16, and a lift plate 17.

The main body 11 is a member to which the bottle 12 is connected and the hood 13 is attached. The bottle 12 collects milk. The hood 13 is fitted to a breast. The main body 11 is a molded product of a synthetic resin material that is hard and light in weight. Specifically, the main body 11 is formed from a synthetic resin material such as polypropylene, polycarbonate, polycycloolefin, polyethersulfone, and/or polyphenylsulfone.

Figure 2:
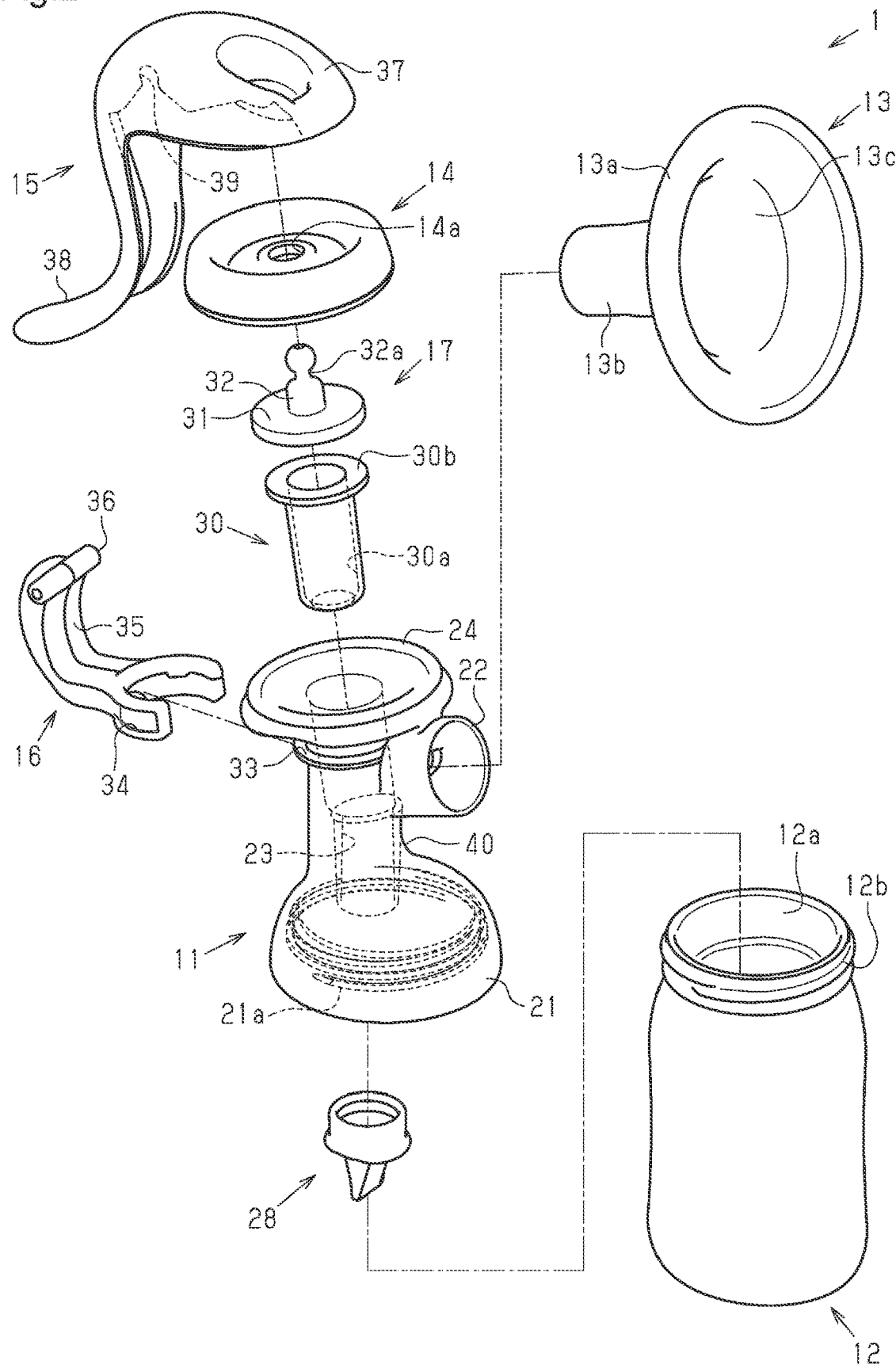
FIG. 2 is an exploded perspective view of the breast pump shown in FIG. 1.

As shown in FIG. 2, the main body 11 includes a bottle attaching portion 21, a hood attaching portion 22, and an internal passage 23. The bottle attaching portion 21 is located toward a lower side of the main body 11 than the hood attaching portion 22. The bottle 12 is a container that collects milk and includes an open bottle portion 12a connected to the bottle attaching portion 21. An external thread 12b is formed in the outer circumferential surface of the circumferential wall of the open bottle portion 12a. When an artificial nipple is attached to the open bottle portion 12a instead of the main body 11, the bottle 12 can be used as a feeding bottle. The bottle attaching portion 21 includes a recess allowing the open bottle portion 12a to be fastened therein. The inner circumferential surface of the bottle attaching portion 21 defining the recess includes an internal thread 21a that can be mated with the external thread 12b.

The hood attaching portion 22 is cylindrical. The hood 13 is dome-shaped or horn-shaped in correspondence with the shape of a breast. The hood 13 includes a large-diameter portion 13a and a cylindrical portion 13b. The large-diameter portion 13a is fitted to a breast. The cylindrical portion 13b is arranged at the peak of the large-diameter portion 13a. The large-diameter portion 13a includes a milking port 13c. In the large-diameter portion 13a, an elastic pad or the like is attached to the edge of the open end so that the large-diameter portion 13a can be tightly fitted to the breast. The cylindrical portion 13b is inserted into and fitted in the hood attaching portion 22.

Figure 3:
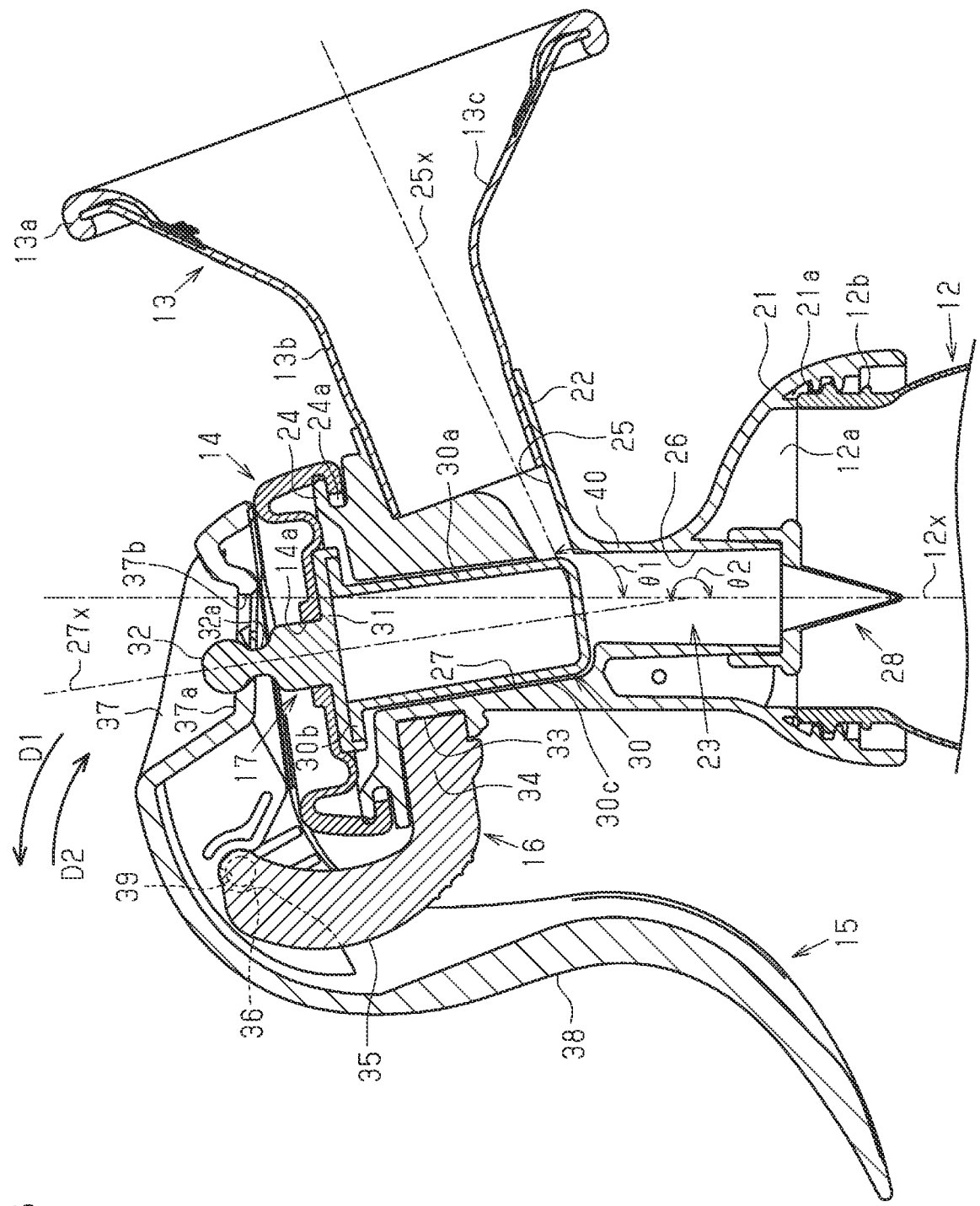
FIG. 3 is a cross-sectional view of the breast pump shown in FIG. 1 in a state in which an internal passage is in a normal pressure state.

As shown in FIG. 3, the internal passage 23 is arranged inside the main body 11. The internal passage 23 extends between and connects the bottle attaching portion 21 to the hood attaching portion 22. Also, the internal passage 23 extends between and connects the bottle attaching portion 21 and the hood attaching portion 22 to an attachment end 24 where and the diaphragm 14 is attached. The internal passage 23 includes an inflow passage 25, a temporary reservoir 26, and a negative pressure generation passage 27.

The inflow passage 25 connects the hood attaching portion 22 and the temporary reservoir 26. The inflow passage 25 is located at the inner side of the hood attaching portion 22 and extends downward to the temporary reservoir 26. The temporary reservoir 26 is located at the inner side of the bottle attaching portion 21 and extends downward. The temporary reservoir 26 is an open area for temporarily collecting the milk flowing from the inflow passage 25 when negative pressure is generated. For example, the temporary reservoir 26 is lies along a bottle axis 12x. The bottle axis 12x is parallel to the center axis of the bottle 12 that extends in a height direction (up-down direction) of the bottle 12 when attached to the bottle attaching portion 21. In an example, the centerline of the temporary reservoir 26 coincides with the bottle axis 12x. The lower end of the temporary reservoir 26 faces the open bottle portion 12a in a state in which the bottle 12 is attached to the bottle attaching portion 21. The angle of the inflow passage 25 with respect to the temporary reservoir 26, that is, the angle θ1 of the center line 25x of the inflow passage 25 with respect to the bottle axis 12x of the temporary reservoir 26, is the angle at which milk flows from the inflow passage 25 into the temporary reservoir 26.

A valve member 28 is attached to the lower end of the temporary reservoir 26 inside the open bottle portion 12a The valve member 28 is a check valve, for example, a duckbill valve. The valve member 28 checks backflow of milk and air from the bottle 12 to the main body 11. Also, the valve member 28 partitions the internal passage 23 and the interior space of the bottle 12 to form a negative pressure state in the internal passage 23. The valve member 28 is formed from a synthetic resin material that is flexible and elastic, such as silicone rubber and/or elastomer, or natural rubber.

The valve member 28 includes a pair of flexible flaps, and a slit is formed between the flaps. When the internal passage 23 is in a negative pressure state, the flaps of the valve member 28 abut each other and close the slit. This closes the lower end of the temporary reservoir 26 to temporarily collect the milk flowing from the inflow passage 25. When the pressure of the internal passage 23 becomes normal, the flaps separate from each other and open the slit. This connects the temporary reservoir 26 and the inside of the bottle 12 so that the milk collected in the temporary reservoir 26 flows into the bottle 12.

The negative pressure generation passage 27 is separate from the inflow passage 25 and branched off from the temporary reservoir 26. Specifically, the negative pressure generation passage 27 extends upward from the upper end of the temporary reservoir 26 or the outlet of the inflow passage 25 leading to the temporary reservoir 26. In an example, the negative pressure generation passage 27 is larger than the inflow passage 25 in diameter. Further, in an example, the negative pressure generation passage 27 is larger than the temporary reservoir 26 in diameter. The negative pressure generation passage 27 has a diameter allowing a user to insert, for example, a finger. The angle of the negative pressure generation passage 27 with respect to the temporary reservoir 26, that is, the angle θ2 of the center axis 27x of the negative pressure generation passage 27 with respect to the bottle axis 12x of the temporary reservoir 26 is set so that milk does not flow backward toward the diaphragm 14. The negative pressure generation passage 27 is tilted at the side of the temporary reservoir 26 opposite the inflow passage 25. The upper end of the negative pressure generation passage 27 corresponds to the attachment end 24 where the diaphragm 14 is attached. The attachment end 24 is flanged and extends outward to increase the area of the opening. Further, the outer circumferential surface of the attachment end 24 includes an attachment groove 24a for attachment of the diaphragm 14.

The diaphragm 14 is a negative pressure generation member that causes the pressure of the internal passage 23 to become negative. The diaphragm 14 is formed from a synthetic resin material that is flexible and elastic such as silicone rubber and/or elastomer, or natural rubber. The diaphragm 14 is engaged with the attachment groove 24a to close the attachment end 24. The internal passage 23 includes three ends, namely, the end of the inflow passage 25 where the hood 13 is attached, the lower end of the temporary reservoir 26 where the valve member 28 is attached, and the attachment end 24. When the hood 13 is fitted to a breast and the milking port 13c is closed, that is, the end of the inflow passage 25 is closed, the other ends, which are the lower end of the temporary reservoir 26 and the attachment end 24, are respectively closed by the valve member 28 and the diaphragm 14. Thus, the internal passage 23 becomes a substantially sealed space. The lift plate 17 is arranged at the inner side of the diaphragm 14 and serves as a connecting portion that connects to the handle 15.

The lift plate 17 is a molded body of a synthetic resin material that is harder than the diaphragm 14. The lift plate 17 is formed from a synthetic resin material such as polycarbonate, polycycloolefin, polyethersulfone, and/or polyphenylsulfone. The lift plate 17 is a portion connecting the handle 15 and includes a plate portion 31 and a connection projection 32. The plate portion 31 is arranged on the inner surface of the diaphragm 14. The connection projection 32 projects from a central part of the surface of the plate portion 31 that faces the diaphragm 14. The central part of the diaphragm 14 includes a through hole 14a through which the connection projection 32 projects outward from the diaphragm 14. The connection projection 32 has a spherical tip and an engagement groove 32a that is formed in the lower end of the sphere.

An insertion member 30 is attached to the plate portion 31. The insertion member 30 includes a volume reduction portion 30a and an attachment flange 30b. The attachment flange 30b is attached to and overlapped with the plate portion 31. In an example, the attachment flange 30b may be fixed to the plate portion 31 with an adhesive or the like. Alternatively, the outer circumferential portion of the attachment flange 30b may be engaged with an engagement piece arranged on the plate portion 31. Furthermore, the attachment flange 30b may be integrated with the plate portion 31 by a welding process such as ultrasonic welding or heat-welding. The volume reduction portion 30a is a cylindrical portion projecting from the attachment flange 30b.

The volume reduction portion 30a is inserted into the negative pressure generation passage 27 to reduce the volume of the negative pressure generation passage 27. The volume reduction portion 30a has a diameter such that a gap 30c is formed between the outer circumferential surface of the volume reduction portion 30a and the inner circumferential surface of the negative pressure generation passage 27. The volume reduction portion 30a projects from the attachment flange 30b and is inserted into the interior space of the negative pressure generation passage 27. The projecting shape of the volume reduction portion 30a corresponds to the internal shape of the negative pressure generation passage 27, into which the volume reduction portion 30a is inserted. In an example, the volume reduction portion 30a is a projection portion that has the form of a column or a cylinder with a closed end. In an example, the negative pressure generation passage 27 has the form of a hollow cylinder and includes an interior space. The volume reduction portion 30a is set to have an outer diameter that is smaller than the inner diameter of the negative pressure generation passage 27.

When the negative pressure generation passage 27 is inserted, the gap 30c allows the volume reduction portion 30a to smoothly move upward and downward even if the volume reduction portion 30a is slightly tilted with respect to the negative pressure generation passage 27. Further, the volume reduction portion 30a has a length set such that the volume reduction portion 30a will not close the outlet of the inflow passage 25 leading to the temporary reservoir 26 when the diaphragm 14 is lifted. Thus, when negative pressure is generated, milk flows from the inflow passage 25 into the temporary reservoir 26. The volume reduction portion 30a has a length set such that the volume reduction portion 30a will be located at the outlet of the inflow passage 25 or the upper end of the temporary reservoir 26 when the diaphragm 14 is not deformed.

The handle 15 is supported by the handle base 16 and pivots relative to the main body 11. The handle base 16 is attached in a rotatable manner to a cylindrical bottom part of the attachment end 24. The handle base 16 is rotatable about the base part of the attachment end 24 in a circumferential direction within a range excluding the hood attaching portion 22, which is for attachment of the hood 13.

The handle base 16 includes an attachment portion 34 and a pivot support piece 35. The attachment portion 34 is C-shaped. The bottom part of the attachment end 24 is cylindrical and includes a groove-like guide portion 33 extending in the circumferential direction. The attachment portion 34 is fitted to the guide portion 33 in a manner rotatable in the circumferential direction. The rotation range of the handle base 16 is limited to the range described above by having the ends of the C-shaped attachment portion 34 come into contact with the ends of the guide portion 33. The pivot support piece 35 is a curved elongated piece extending upward from the attachment portion 34 such that the distal end of the pivot support piece 35 is located upward of the diaphragm 14. The distal end of the pivot support piece 35 includes a pivot shaft 36 that pivotally supports the handle 15.

The handle 15 is formed from a synthetic resin material such as polycarbonate, polycycloolefin, polyethersulfone, and/or polyphenylsulfone. The handle 15 includes a lifter 37 and a lever 38. The lifter 37 pulls the diaphragm 14 using the lift plate 17 and includes a pit 37a. The bottom surface of the pit 37a includes an engagement hole 37b. The connection projection 32 of the lift plate 17 is inserted through the engagement hole 37b so that the edge of the engagement hole 37b engages the engagement groove 32a In this manner, the handle 15 is connected to the diaphragm 14 by the lift plate 17 so that the diaphragm 14 can be lifted. Further, the handle 15 is rotatable relative to the connection projection 32.

The lever 38 extends downward and toward the bottle 12 and is used as a grip. The handle 15 has a curved outer surface to allow for easy handling and is held by the user with fingers other than the thumb. The lever 38 is gradually curved outward. A shaft support 39 is arranged at the inner side of the handle 15 near the boundary between the lever 38 and the lifter 37 and engaged with the pivot shaft 36. When the pivot shaft 36 is pivotally engaged with the shaft support 39, the handle 15 is supported and pivots relative to the main body 11. This portion serves as a fulcrum where the handle 15 is moved back and forth. The handle 15 is manually pivoted in arrowed direction D1 that is a pivot operation direction, and the handle 15 is pivoted by the resiliency of the diaphragm 14 in arrowed direction D2 that is a recovery direction.

The main body 11 includes a recess 40 below the hood attaching portion 22 opposing the handle 15. The recess 40 engages the base of the thumb of the user. Specifically, in the breast pump 1, the user places fingers other than the thumb on the lever 38 with the base of the thumb engaged with the recess 40 to squeeze the handle 15 and pivot the handle 15 about the pivot shaft 36.

The direction in which the handle 15 lifts the diaphragm 14 using the lift plate 17 is perpendicular to the main surface of the diaphragm 14. That is, the handle 15 lifts the diaphragm 14 using the lift plate 17 in arrowed direction D1 intersecting the bottle axis 12x rather than the direction in which the bottle axis 12x extends. This allows the gap 30c to be reduced and the volume of the internal passage 23 to be decreased.

The operation of the breast pump 1 will now be described.

The breast pump 1 is assembled as described below. The valve member 28 is attached to the temporary reservoir 26 of the main body 11. The lift plate 17 is integrated with the insertion member 30, and the volume reduction portion 30a is inserted into the negative pressure generation passage 27. The connection projection 32 is inserted through the through hole 14a, and the diaphragm 14 is attached to the attachment end 24. The handle base 16 is attached to the guide portion 33 of the main body 11. The connection projection 32 is inserted through the engagement hole 37b of the handle 15, and the edge of the engagement hole 37b is engaged with the engagement groove 32a. Further, the pivot shaft 36 of the handle base 16 is engaged with the shaft support 39 of the handle 15. The bottle 12 is attached to the bottle attaching portion 21 of the main body 11, and the hood 13 is attached to the hood attaching portion 22.

Figure 4:
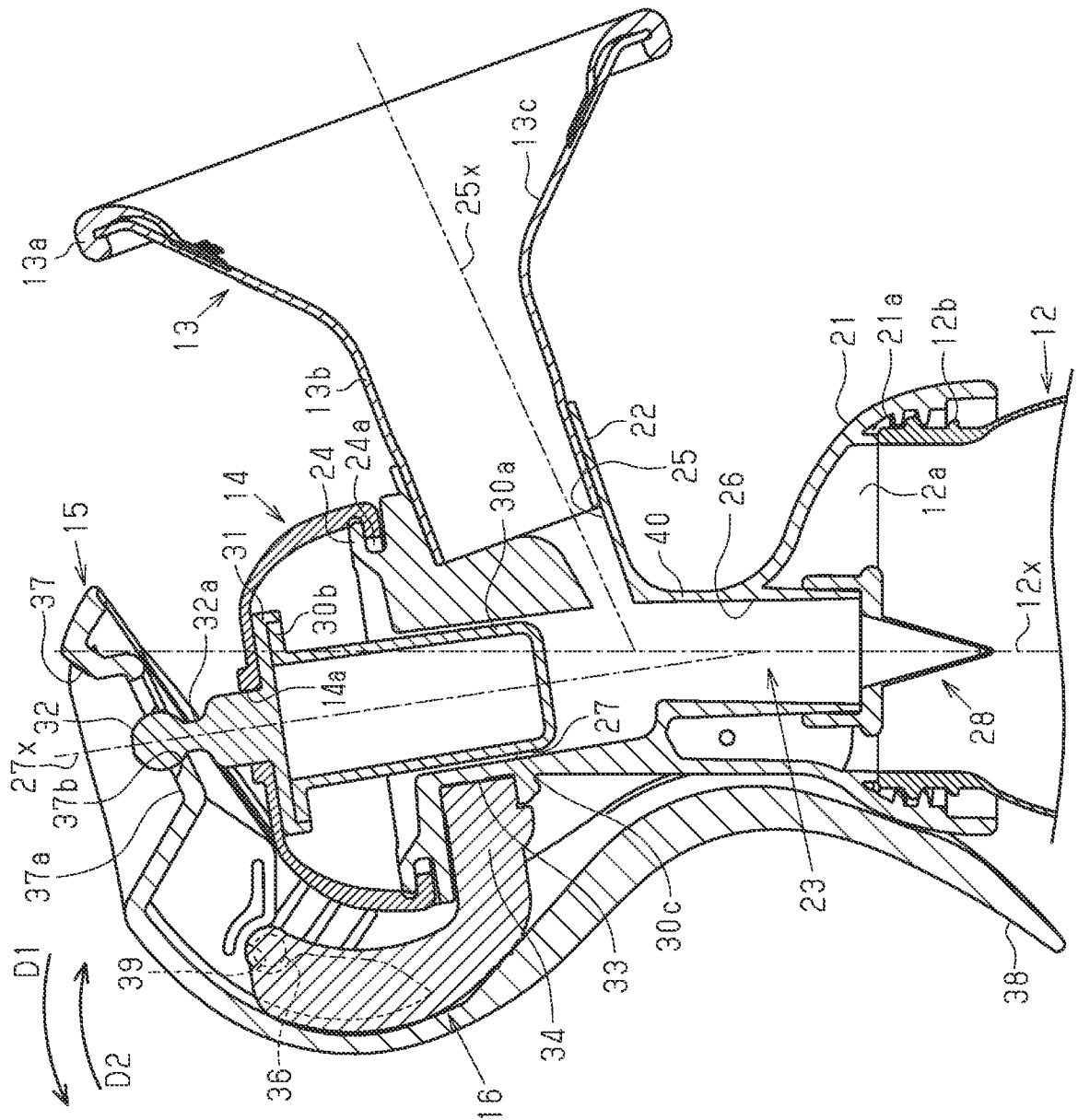
FIG. 4 is a cross-sectional view of the breast pump shown in FIG. 1 in a state in which the internal passage is in a negative pressure state.

As shown in FIG. 1 and FIG. 4, when pumping milk, the user holds the breast pump 1 by placing fingers other than the thumb on the handle 15 with the base of the thumb engaged with the recess 40 of the main body 11. Then, the hood 13 is fitted to the breast of the user so as to close the milking port 13c. As a result, the internal passage 23 becomes a substantially sealed space. In this case, the handle base 16 is guided by the guide portion 33 and the handle 15 is rotated about the connection projection 32 relative to the main body 11 in conformance with the body of the user or the like. This allows for easy handle operation by the user.

The handle 15 lifts the diaphragm 14 using the lift plate 17 when the handle 15 is manually pivoted in arrowed direction D1, in which the lever 38 approaches the side surface of the bottle 12. In this case, the volume reduction portion 30a is also lifted inside the negative pressure generation passage 27. This forms a negative pressure state in the internal passage 23, and pumped milk flows from the inflow passage 25 into the temporary reservoir 26. In a negative pressure state, the bottom of the temporary reservoir 26 is closed by the valve member 28. Accordingly, the milk flowing from the inflow passage 25 collects in the temporary reservoir 26.

When the user reduces the squeezing force, the resiliency of the diaphragm 14 pivots the handle 15 in arrowed direction D2 and returns the internal passage 23 to normal pressure. This opens the valve member 28 of the temporary reservoir 26, and milk flows into the bottle 12. The handle 15 is repetitively moved back and forth to pump milk. In this case, the volume reduction portion 30a is also reciprocated inside the negative pressure generation passage 27.

Although the negative pressure generation passage 27 has a relatively large diameter and increases the volume of the internal passage 23, insertion of the volume reduction portion 30a, which is integrated with the lift plate 17, decreases the volume of the internal passage 23. Thus, the pressure that changes when the diaphragm 14 is deformed is subtly affected.

After use, the breast pump 1 is disassembled as shown in FIG. 2 for cleaning. Specifically, the bottle 12, the hood 13, the handle 15, the handle base 16, the diaphragm 14, and the lift plate 17, which is integrated with the volume reduction portion 30a, are removed from the main body 11. Then, each part is cleaned with a hand or scrubbed with a brush. In particular, the negative pressure generation passage 27 of the internal passage 23 in the main body 11 has a diameter allowing for insertion of a finger. Therefore, the negative pressure generation passage 27 can be thoroughly cleaned with a finger or a brush. After cleaning, the breast pump 1 is assembled as described above.

The breast pump 1 has the advantages described as below.

(1) Even though the diameter of the negative pressure generation passage 27 is increased to allow the internal passage 23 to be cleaned easily, the volume reduction portion 30a is inserted into the negative pressure generation passage 27, which has a relatively large diameter. Thus, the volume of the internal passage 23 is not increased, and decreases in the milk-pumping efficiency are minimized.

(2) The insertion member 30 is fixed to and integrated with the lift plate 17 as a single component. This facilitates processes like cleaning and assembling/disassembling.

(3) The volume reduction portion 30a is reciprocated inside the negative pressure generation passage 27 in accordance with the pivoting operation of the handle 15.

(4) The gap 30c is reduced between the outer circumferential surface of the volume reduction portion 30a and the inner circumferential surface of the negative pressure generation passage 27. This allows the negative pressure generation passage 27 to be increased in diameter without increasing the volume of the negative pressure generation passage 27.

(5) The gap 30c allows for smooth movement of the volume reduction portion 30a inside the negative pressure generation passage 27 even when the volume reduction portion 30a is inserted in the negative pressure generation passage 27. Accordingly, the handle 15 is smoothly pivoted by a manual operation.

The above-described embodiment may be modified as follows.

Figure 5:
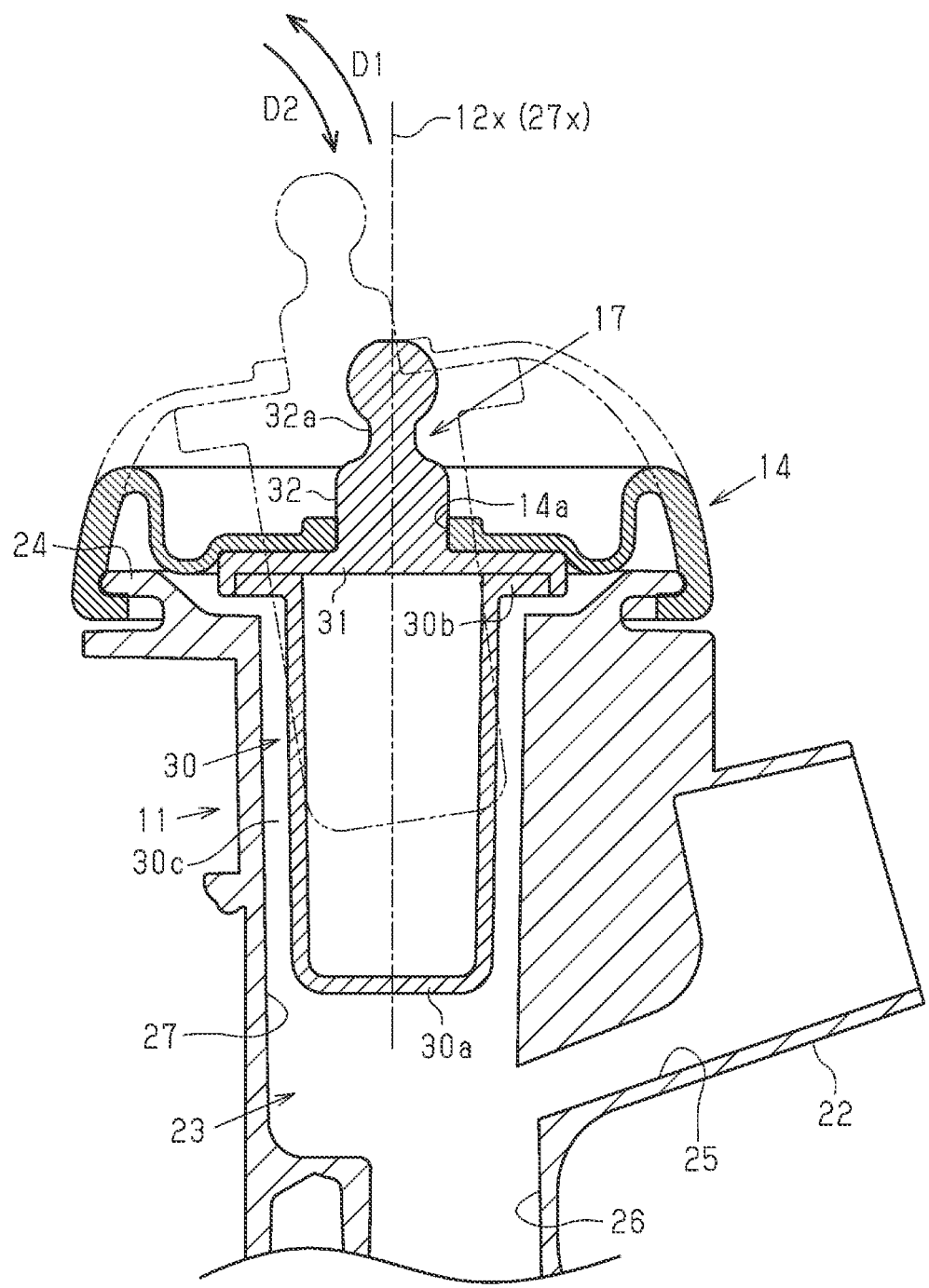
FIG. 5 is a diagram showing a modified example of a negative pressure generation passage and a volume reduction portion.

As shown in FIG. 5, the negative pressure generation passage 27 may be arranged so that the center axis 27x coincides with the bottle axis 12x. In this case, the direction in which the volume reduction portion 30a is moved corresponds to arrowed direction D1 that intersects the bottle axis 12x. Thus, the volume reduction portion 30a will be tilted inside the negative pressure generation passage 27. Accordingly, the gap 30c between the outer circumferential surface of the volume reduction portion 30a and the inner circumferential surface of the negative pressure generation passage 27 is set to be greater than that of the above embodiment. This allows the volume reduction portion 30a to be smoothly moved in the negative pressure generation passage 27 even when tilted and reciprocated.

Figure 6:
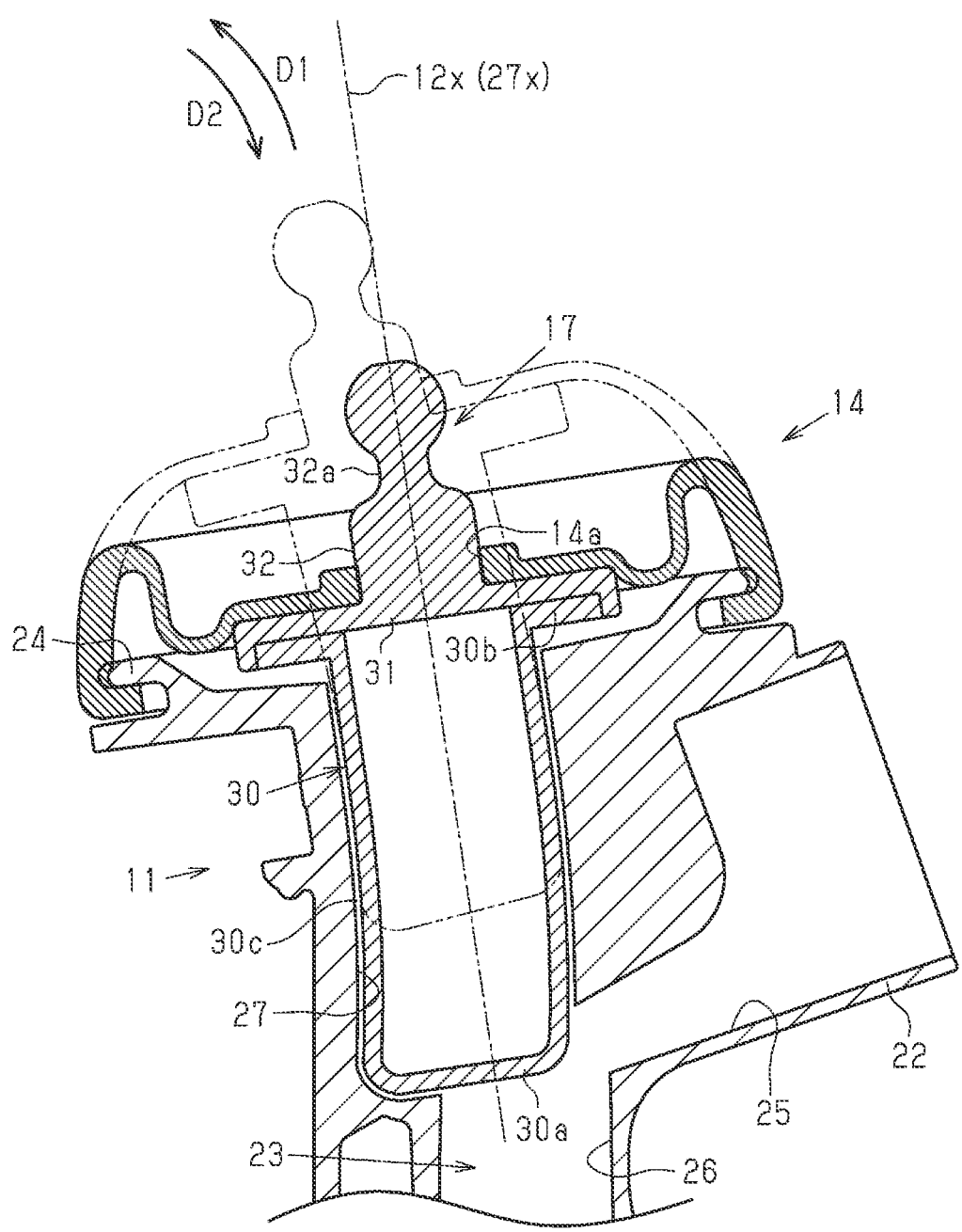
FIG. 6 is a diagram showing a modified example of a negative pressure generation passage and a volume reduction portion.

As shown in FIG. 6, the volume reduction portion 30a is moved in arrowed direction D1 that intersects the bottle axis 12x. The volume reduction portion 30a may be curved along arrowed direction D1, and the negative pressure generation passage 27 may be curved along arrowed direction D1 in correspondence with the shape of the volume reduction portion 30a. This reduces the gap 30c between the outer circumferential surface of the volume reduction portion 30a and the inner circumferential surface of the negative pressure generation passage 27 from that shown in FIG. 5. When the gap 30c is reduced, the volume reduction portion 30a further effectively reduces the volume of the internal passage 23.

The lift plate 17 may be formed integrally with the insertion member 30 as a single component. This decreases the number of parts.

The lift plate 17 may be adhered and fixed to the outer surface of the diaphragm 14. In this case, the volume reduction portion 30a is integrally arranged on the inner surface of the diaphragm 14.

The lift plate 17 may be omitted, and the connection projection 32 may be arranged on the outer surface of the diaphragm 14 as a connecting portion connected to the engagement hole 37b of the handle 15.

The volume reduction portion 30a may be separated from the diaphragm 14. In this case, in an example, the volume reduction portion 30a is connected to the attachment flange 30b by a spacer that maintains a constant distance between the volume reduction portion 30a and the attachment flange 30b. Alternatively, the volume reduction portion 30a is connected to the plate portion 31 of the lift plate 17 by a spacer. In an example, the spacer may be formed by one or more linear members or shafts that connect the volume reduction portion 30a and the attachment flange 30b or the plate portion 31.

The insertion member 30 may be omitted, and the volume reduction portion 30a may be formed integrally with the diaphragm 14 as a single component. This structure also decreases the number of parts.

The distal end surface of the volume reduction portion 30a does not have to be flat and may be, for example, convex or concave.

The outer circumferential surface of the volume reduction portion 30a may have any outer form as long as the volume of the negative pressure generation passage 27 is reduced. For example, in side view, the circumferential surface of the volume reduction portion 30a may be corrugated, concave, or convex.

The projecting shape of the volume reduction portion 30a does not have to correspond to the internal shape of the negative pressure generation passage 27, into which the volume reduction portion 30a is inserted. For example, the projecting shape (outer shape) of the volume reduction portion 30a may be a polygonal post such as a triangular post, a square post, and a hexagonal post, and the negative pressure generation passage 27 may have the form of a hollow cylinder. Alternatively, the projecting shape of the volume reduction portion 30a may be a column or a cylinder, and the internal shape of the negative pressure generation passage 27 may correspond to a polygonal post such as a triangular post, a square post, and a hexagonal post.

The structure of the internal passage 23 is not limited. For example, the temporary reservoir 26 may be omitted. In this case, the valve member 28 may be omitted.

The handle 15 may be directly supported by the main body 11 in a pivotal manner instead of being supported by the handle base 16. In this case, the pivot support piece 35, the pivot shaft 36, and the like are integrated with the main body 11.

The handle 15 may extend toward a user where the hood 13 is located instead of downward toward the bottle 12. In this case, the user can pivot the handle 15 in a supination position with the palm facing upward.

The bottle 12 does not have to be attachable to and detachable from the bottle attaching portion 21 and may be formed integrally with the bottle attaching portion 21. Further, the hood 13 does not have to be attachable to and detachable from the hood attaching portion 22 and may be formed integrally with the hood attaching portion 22.

The inflow passage 25 and the temporary reservoir 26 may also have a diameter allowing a user to insert, for example a finger.

The negative pressure generation passage 27 does not have to be tilted with respect to the temporary reservoir 26.

The lever 38 does not have to be gradually curved outward and may be linear. Alternatively, the lever 38 may have a distal end that is bent toward the main body 11.

REFERENCE SIGNS LIST 1) breast pump, 11) main body, 12) bottle, 12a) open bottle portion, 12b) external thread, 12x) bottle axis, 13) hood, 13a) large-diameter portion, 13b) cylindrical portion, 13c) milking port, 14) diaphragm, 14a) through hole, 15) handle, 16) handle base, 17) lift plate, 21) bottle attaching portion, 21a) internal thread, 22) hood attaching portion, 23) internal passage, 24) attachment end, 24a) attachment groove, 25) inflow passage, 25x) center axis, 26) temporary reservoir, 27) negative pressure generation passage, 27x) center axis, 28) valve member, 30) insertion member, 30a) volume reduction portion, 30b) attachment flange, 30c) gap, 31) plate portion, 32) connection projection, 32a) engagement groove, 33) guide portion, 34) attachment portion, 35) pivot support piece, 36) pivot shaft, 37) lifter, 37a) pit, 37b) engagement hole, 38) lever, 39) shaft support, 40) recess.

The invention claimed is:

1. A breast pump, comprising:
 a main body including:
  a hood attaching portion to which a hood, configured to be fitted to a breast and including a milking port, is attached;
  a bottle attaching portion to which a bottle for collecting milk is attached;
  an internal passage extending between the hood attaching portion and the bottle attaching portion;
  a diaphragm attached to the internal passage and configured to generate negative pressure in the internal passage;
  a handle that is manually operated;
  a connecting portion connecting the diaphragm and the handle and configured to displace the diaphragm in a lifting direction in accordance with movement of the handle; and
  a volume reduction portion inserted into the internal passage and configured to reduce a volume of the internal passage, wherein the connecting portion includes a lift plate that includes:
   a plate portion arranged on an inner surface of the diaphragm; and
   a connection projection connected with the handle, the connection projection extending from the plate portion through the diaphragm and projecting out of an outer surface of the diaphragm located at a side opposite to the inner surface, wherein the volume reduction portion is arranged on the plate portion and includes a cylindrical portion projecting from an attachment flange, wherein the internal passage includes a negative pressure generation passage that is closed by the diaphragm and has a form of a hollow cylinder, and wherein the volume reduction portion has a shape corresponding to an internal shape of the negative pressure generation passage and is inserted in the negative pressure generation passage.

2. The breast pump according to claim 1, wherein the handle is pivotally attached to the main body, and wherein the handle is configured to lift the diaphragm using the connecting portion in a direction intersecting a bottle axis that extends in a height direction of the bottle.

3. The breast pump according to claim 1, wherein the breast pump includes a gap formed between an inner circumferential surface of the negative pressure generation passage and an outer circumferential surface of the volume reduction portion.

4. The breast pump according to claim 1, wherein the breast pump comprises:
  an insertion member that includes the volume reduction portion and the attachment flange, wherein the attachment flange is attached to and overlapped with the plate portion of the lift plate.

* * * * *